United States Patent [19]

Wirth et al.

[11] 4,210,595

[45] Jul. 1, 1980

[54] PROCESS FOR THE PRODUCTION OF ORGANO-TIN COMPOUNDS

[75] Inventors: Hermann O. Wirth, Bensheim; Hermann W. Wehner, Zwingenberg, both of Fed. Rep. of Germany

[73] Assignee: Ciba-Geigy Corporation, Ardsley, N.Y.

[21] Appl. No.: 24,846

[22] Filed: Mar. 28, 1979

Related U.S. Application Data

[62] Division of Ser. No. 900,546, Apr. 27, 1978, Pat. No. 4,158,669.

[30] Foreign Application Priority Data

May 6, 1977 [CH] Switzerland .............. 5708/77
Nov. 9, 1977 [CH] Switzerland .............. 13665/77

[51] Int. Cl.$^2$ .............................................. C07F 7/22
[52] U.S. Cl. .................................................. 260/429.7
[58] Field of Search ...................................... 260/429.7

[56] References Cited

U.S. PATENT DOCUMENTS

| 3,412,122 | 11/1968 | Considine et al. | 260/429.7 |
| 3,440,255 | 4/1969 | Matsuda | 260/429.7 |
| 3,607,893 | 9/1971 | Reifenberg | 260/429.7 |
| 4,105,684 | 8/1978 | Hutton et al. | 260/429.7 |
| 4,130,573 | 12/1978 | Hutton et al. | 260/429.7 |

OTHER PUBLICATIONS

Rappoport, The Chemistry of the Cyano Group Interscience, pp. 264–265 (1970).

*Primary Examiner*—Helen M. S. Sweed
*Attorney, Agent, or Firm*—Luther A. R. Hall

[57] ABSTRACT

The direct reaction of metallic tin with an $\alpha,\beta$-unsaturated nitrile, hydrogen chloride, hydrogen bromide or hydrogen iodide in the presence of an alcohol yields diorgano-tin dihalides with an iminoester function in the organo groups. This iminoester function can be converted with mercaptans into the corresponding iminothioester function. The novel diorgano-tin dihalides of the formula

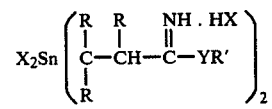

wherein
X represents a chlorine, bromine or iodine atom,
Y represents an oxygen or sulphur atom,
R represents a hydrogen atom and/or alkyl, and
R' represents a hydrocarbon group of aliphatic or aromatic character which can contain functional groups, are, for example, valuable intermediates for the production of PVC stabilisers.

10 Claims, No Drawings

PROCESS FOR THE PRODUCTION OF ORGANO-TIN COMPOUNDS

This is a divisional of application Ser. No. 900,546, filed on Apr. 27, 1978, now U.S. Pat. No. 4,158,669, issued on June 19, 1979.

The present invention relates to carbofunctional organotin compounds, a process for their production and the use thereof.

Organo-tin compounds are of considerable economic interest as stabilisers for halogen-containing thermoplastics. Recently, carbofunctional organo-tin compounds have also been proposed for this purpose. There are various possibilities of producing such stabilisers.

For example German Offenlegungsschrift 1,963,569 discloses in general terms that halostannic acid reacts in the presence of polar solvents with olefins which can contain functional groups. Acrylonitrile is cited by way of example. It has been found, however, that in this reaction the desired compound is obtained in only unsatisfactory yield. Moreover, only monoorgano-tin compounds can be produced by this process.

Monoorgano-tin compounds which contain a β-carbonylethyl group are also only obtained by a process described in German Offenlegungsschrift 2,540,210. They are produced by the reaction of tin dihalide with hydrogen halide and a corresponding olefin.

A similar process, but for the production of diorgano-tin compounds, is described in German Offenlegungsschrift 2,607,178. However, this process is restricted to those olefins which contain a carbonyl group in conjugation to the double bond, and it cannot be applied as a matter of course to other substituted vinyl compounds, for example nitriles.

There is however interest in economic processes for the production of diorgano-tin derivatives using easily obtainable starting compounds, whereby new compounds can also be obtained.

It is one object of the present invention to provide an economic process for the production of new carbofunctional organo-tin compounds.

Accordingly, the present invention provides a process for the production of organo-tin compounds of the formula

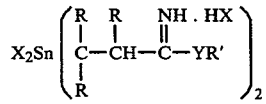

wherein

X represents a chlorine, bromine or iodine atom,

Y represents an oxygen or sulphur atom,

R represents a hydrogen atom and/or alkyl, and

R' represents a hydrocarbon group of aliphatic or aromatic character which can contain functional groups, by the direct reaction of metallic tin with an olefin and hydrogen chloride, hydrogen bromide or hydrogen iodide, which process comprises reacting, as olefin, an unsaturated nitrile of the formula

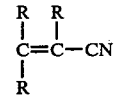

wherein R has the given meaning, in the presence of an alcohol R'OH and, for the production of the iminothioesters (Y=S), reacting the resulting iminoesters with a mercaptan R'SH.

The invention also relates to the organo-tin compounds of the given formula. These compounds can also be described by way of a zwitterion formulation, containing 4 halogen atoms at the tin and positively charged NH₂ groups. The compounds of the present invention are designated as iminoesters or also iminoester hydrochlorides.

For predominantly economic reasons, X represents a chlorine atom. R is preferably hydrogen and/or methyl, especially hydrogen, this preference arising from the easily obtainable nitriles, viz. acrylonitrile, methacrylonitrile, crotonitrile and β-dimethylacrylonitrile.

R' as hydrocarbon group can be: linear or branched alkyl, unsubstituted or substituted cycloalkyl, cycloalkylalkyl, aryl and aralkyl, the preferred substituent being alkyl which can contain functional groups. Cycloalkyl is preferably cyclohexyl, aryl is phenyl and aralkyl is benzyl. R' preferably contains 1 to 12 carbon atoms and represents especially cycloalkyl or linear or branched alkyl.

If R' is substituted by functional groups, these groups are for example hydroxyl, thiol, alkoxy, alkylthio, carboxyl and carbalkoxy.

Examples of R' are: methyl, ethyl, n-propyl or isopropyl, n-butyl, isobutyl and tert-butyl, pentyl, hexyl, heptyl, 2-hexyl, 3-heptyl, octyl, 2-ethylhexyl, nonyl, decyl, undecyl, dodecyl, cyclopentyl, cyclohexyl, methylcyclohexyl, cyclohexylmethyl, methylcyclohexylmethyl, phenyl, methylphenyl, ethylphenyl, butylphenyl, octylphenyl, naphthyl, benzyl, methylbenzyl, octylbenzyl, α-or β-phenylethyl.

Examples of R' containing functional groups are: β-hydroxyethyl, β-mercaptoethyl, methoxyethyl, butoxyethyl, octoxyethyl, methylthioethyl, propylthioethyl, carboxymethyl, β-carboxyethyl and carboalkoxyalkyl, for example carbomethoxymethyl, carboethoxypropyl, carbobutoxyethyl, carbododecyloxymethyl.

In the process of the invention, the metallic tin can be used in different form, for example as powder, filings, granulate, tin dust or tin plate.

It is also possible to carry out the reaction in an excess of reactants (alcohol and/or nitrile) or in an additional solvent. Suitable solvents are inert solvents, for example those with keto, acid amide, ether, carboxylate, sulphoxide or sulphone functions, or hydrocarbons, halogenated hydrocarbons, for example tetrahydrofuran, dimethyl formamide, dimethyl sulphoxide, toluene and chloroform.

In the reaction of the present invention, it is important that, in addition to the unsaturated nitrile, an alcohol is present, preferably in at least molar ratio, which can be about 1:1 to 1:1.2.

The reaction temperature is in general between −30° and +150° C., preferably between 20° and 90° C. The reaction is advantageously carried out under normal or slight excess pressure.

The procedure is that the hydrogen halide (preferably HCl) is introduced into the reaction vessel containing the tin and the reactants, with or without solvent.

It is however also possible to charge the reaction vessel with the tin in the solvent and to add the reactants and hydrogen halide gas simultaneously. In this case, it is advantageous to proceed in accordance with the countercurrent principle, by means of which it is also possible to carry out the process continuously.

The iminoesters of the present invention can be converted into the corresponding iminothioesters by reaction with mercaptans.

The reaction of the iminoesters with mercaptans can be carried out in the solvents referred to previously. On occasion, the mercaptan can also be used as solvent. In general, stoichiometric ratios are maintained. The catalysts conventionally used for transesterification reactions can be used for the reaction, for example protons or Lewis acids. However, the reaction can also be carried out without a catalyst. The process is preferably carried out in the presence of gaseous or dissolved HCl gas. The iminoesters do not need to be isolated beforehand, and the reaction mixture obtained in the first reaction (with alcohol) can be further used direct.

The process of the present invention affords surprisingly valuable organo-tin compounds in high yields in simple and economic manner and under very mild reaction conditions. Easily obtainable and cheap products can be used as starting materials.

No problems are encountered in isolating the desired diorgano-tin compounds. However, it is also possible to carry out the reaction such that mixtures of such diorgano-tin compounds with the corresponding monoorgano-tin compounds are obtained. These mixtures can contain up to 30% by weight and more of monoorgano-tin compound.

The organo-tin compounds of the present invention are amorphous or crystalline solids or liquid to highly viscous or partially resin-like substances which are colourless and partly water-soluble or soluble in organic solvents. They are preeminently suitable for use as effective biocides. They are also suitable as catalysts or catalyst components for the production of polyurethanes.

Finally, the compounds of the invention can be used as intermediates for the production of stabilisers for halogencontaining thermoplastics. For example, organo-tin compounds of the kind described in German Offenlegungsschrift 2,607,178 can be obtained by hydrolysis, and can in turn be converted into stabilisers by the methods described therein.

The invention is described in more detail by the following Examples, in which the parts are by weight.

EXAMPLE 1

A three-necked flask equipped with stirrer, reflux cooler and bubble counter is charged at 20° C. with 118 parts of tin powder, 106 parts of acrylonitrile and 92 parts of abs. ethanol in 200 parts of dimethoxy ethane. With stirring, a flow of dry hydrogen chloride gas is passed through the mixture and so regulated that absorption just occurs. The reaction temperature rises to between 30° and 40° C. After about 4 hours, the tin has reacted virtually quantitatively. Hydrogen chloride gas is introduced for a further ½ hour, whereupon a dense slurry forms. After addition of dimethoxy ethane, the precipitate is collected by filtration, then washed with methylene chloride and dried in a high vacuum at 35° C., affording 277 parts of a colourless powder which melts with decomposition (evolution of gas) at 161°–164° C. Analysis shows the compound to have the structure $$\left[ Cl_2Sn(CH_2CH_2C \underset{OC_2H_5}{\overset{\displaystyle \nearrow NH_2^{\oplus}Cl^{\ominus}}{\nwarrow}} \right]_2$$

|  | Sn (%) | Cl (%) |
|---|---|---|
| Found | 26.7 | 30.3 |
| Theory | 25.7 | 30.7 |

[1]NMR spectrum in dimethyl sulphoxide as against tetramethylsilane as internal standard:

|  | $CH_3-CH_2-O-$ | $-CH_2-Sn-$ | $-CH_2-CH_2-Sn-$ | $CH_3-CH_2-O$ |
|---|---|---|---|---|
| chemical displacement (ppm) | 1.35 (tripl.) | 1.70 (mult.) | 2.98 (mult.) | 4.35 (quart.) |
| intensity | 3 | 2 | 2 | 2 |

[1]NMR spectrum in dimethyl sulphoxide as against tetramethylsilane as internal standard:

Comparison Example

A three-necked flask equipped with stirrer, reflux cooler and bubble counter is charged at 20° C. with 28 parts of tin filings and 27 parts of acrylonitrile in 80 parts of dimethoxy ethane. With stirring, a flow of dry hydrogen chloride gas is passed through the mixture. The reaction temperature is between 30° and 40° C. The reaction comes to a halt after 2 hours (tin consumption:41%). In comparison to Example 1, it is clearly seen that the additional use of an alcohol effects a substantially higher consumption of tin.

EXAMPLES 2–7

The reactants listed in the following table are reacted in accordance with Example 1. Deviations from the procedure are indicated in the foot notes. The Sn(II) content is determined in the filtrates.

Table

| Example | Alcohol | Solvent | Reaction time [h][1] | tin reaction | tin(II)[2] content [%] | Resulting tin compound |
|---|---|---|---|---|---|---|
| 2[3] | ethanol | dimethoxy ethane | 4.0 | 100 | traces | $Cl_2Sn(CH_2CH_2C{\overset{NH \cdot HCl}{\underset{OC_2H_5}{\diagup}}})_2$<br>m.p. 161°–164° C., decomposition |
| 3[4] | ethanol | dimethoxy ethane | 5.0 | 100 | ~10 | $Cl_2Sn(CH_2CH_2C{\overset{NH \cdot HCl}{\underset{OC_2H_5}{\diagup}}})_2$ [5] |
| 4[4] | ethanol | dimethoxy ethane[6] | 5.0 | 100 | traces | $Cl_2Sn(CH_2CH_2C{\overset{NH \cdot HCl}{\underset{OC_2H_5}{\diagup}}})_2$ |
| 5[7] | ethanol | dimethoxy ethane | 4.0 | 100 | 0.2 | $Cl_2Sn(CH_2CH_2C{\overset{NH \cdot HCl}{\underset{OC_2H_5}{\diagup}}})_2$ [8] |
| 6 | methanol | diglyme | 3.5 | 100 | — | $Cl_2Sn(CH_2CH_2C{\overset{NH \cdot HCl}{\underset{OCH_3}{\diagup}}})_2$ [9]<br>m.p. 255°–258° C., decomposition |
| 7 | n-butanol | diglyme | 3.5 | 100 | — | $Cl_2Sn(CH_2CH_2C{\overset{NH \cdot HCl}{\underset{OC_4H_9}{\diagup}}})_2$ [10]<br>m.p. 153°–156° C., decomposition |
| 7a | 2-ethyl-hexanol | chloroform | 6.5 | 100 | — | $Cl_2Sn(CH_2CH_2C{\overset{NH \cdot HCl}{\underset{O\text{-}i\text{-}C_8H_{17}}{\diagup}}})_2$<br>m.p. 153°–154° C., decomposition |
| Comparison I[11] | without | dimethoxy ethane | 5.0 | 50 | <0.3 | amber-coloured solid |
| Comparison II[13] | acryl-ester | dimethoxy ethane[6] | 5.0 | 100 | 16.0 | $Cl_2Sn(CH_2CH_2C{\overset{O}{\underset{OCH_3}{\diagup}}})_2$ |
| Comparison III[14] | without | dimethoxy ethane | 2.0 | 41 | traces | Only 6% yield of the compound of Example 2 after special subsequent reaction.[15] |

(1) until the tin has completely dissolved
(2) iodometric determination
(3) tin powder
(4) four-fold excess of acrylonitrile and ethanol at the start, then addition of tin in portions until the full stoichiometric ratio is reached
(5) bis-(carbiminoethoxyethyl) tin dichloride bis-hydrochloride can be readily hydrolysed with water to bis-(carboethoxyethyl) tin dichloride

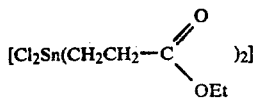

(6) solvent is added after half the reaction time to prevent precipitate forming on the tin filings
(7) tin powder added to dimethoxy ethane and at 0° C. acrylonitrile/ethanol is added dropwise while simultaneously introducing HCl
(8) heating for 1 hour in a high vacuum (120° C.) results in a so-called "Pinner cleavage" to give the carboxy amide derivative according to the equation

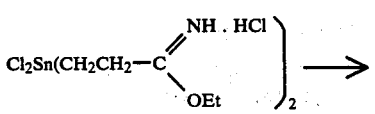

-continued

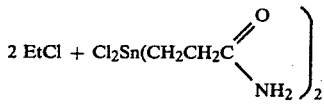

(9) precipitated with $CH_2Cl_2$
(10) precipitated with acetone
(11) direct comparison example to Example 2
(12) became highly viscous after stripping off volatile constituents and solidified to a glassy product which is only partially soluble in MeOH
(13) direct comparison example to Example 4, using methyl acrylate instead of acrylonitrile
(14) batch comparable with comparison I (after 2 hours the reaction comes to a stop; tin reaction about 40%) and the resulting colourless solution is reacted with the stoichiometric amount of ethanol (based on reacted tin)
(15) very low yield of organo-tin iminoester hydrochloride (~6%); it is evident that the alcohol must be present at the start of the reaction in order to obtain sufficient yields.

EXAMPLE 8

The apparatus of Example 1 is charged with 23.14 parts of

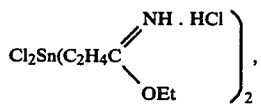

and 10.6 parts of methyl thioglycolate in 150 parts of dimethyl formamide. HCl gas is then introduced into the solution until it is saturated (after about 2 hours). A small amount of precipitated solid is removed by filtration and then volatile constituents are stripped off in vacuo, affording a yellowish viscous oil as residue.

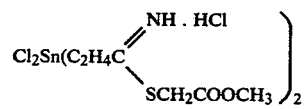

can be detected as main constituent.

EXAMPLE 9

The apparatus of Example 1 is charged with 23.7 parts of tin powder, 21.2 parts of acrylonitrile, 18.4 parts of ethanol and 150 parts of chloroform as solvent. HCl gas is introduced over the course of 5 hours until the solution is saturated. The reaction temperature rises to 35° C. Volatile constituents are stripped off in vacuo, leaving a colourless solid residue

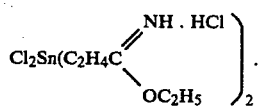

EXAMPLE 10

The starting materials of Example 9 are reacted in the indicated amounts, except that 70 parts of tert-butanol are used as solvent instead of chloroform. The tin powder is added to the chloroform and the mixture is stirred while introducing HCl gas and at the same time slowly adding a mixture of acrylonitrile and ethanol. The temperature rises to 45°–60° C. and the reaction proceeds for 6 hours until the tin has reacted quantitatively. Working up is effected as described in Example 10.

EXAMPLE 11

The procedure of Example 9 is repeated with the sole variation that the reaction vessel is charged with all the starting materials except for ethanol, which is then added dropwise after the introduction of HCl gas. The temperature rises to 40°–45° C. The tin has dissolved after 5 hours and the reaction is complete after 6 hours (HCl saturation). Working up is as previously described, affording the compound of Example 9.

EXAMPLE 12

The procedure of Example 9 is repeated, replacing chloroform by 100 parts of ethyl acetate. The temperature rises to 50°–60° C. and the reaction time is 5 hours. The compound of Example 9 is obtained.

EXAMPLE 13

The reaction of Example 1 is repeated using 100 parts of dimethyl sulphoxide and 70 parts of tetramethylene sulphone respectively instead of chloroform. The reaction temperature is 40°–50° C. and the time taken for all the tin to dissolve is 6 hours. In both cases the compound of Example 9 is isolated.

EXAMPLE 14

The procedure of Example 9 is modified by charging the reaction vessel with tin, ethanol and 70 parts of chloroform. While introducing HCl gas, 30 parts of chloroform are added dropwise. The temperature rises to 55° C. and the reaction time is 4 hours. The solid residue consists of the desired compound.

EXAMPLE 15

The procedure of Example 9 is repeated using diethyl ether as solvent. The reaction is complete after 3 hours at a temperature of 32° C. After working up, the compound of Example 9 is obtained.

EXAMPLE 16

The procedure of Example 9 is repeated using as solvent 100 parts of methyl isobutyl ketone and 100 parts of diisobutyl ketone. The reaction temperature is 70° C. and the time taken until saturation with HCl is complete is 2 hours. $^1$NMR spectrum shows that the solid residue consists in the main of

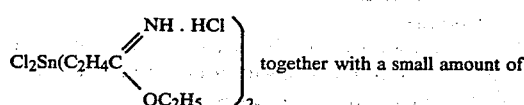 together with a small amount of

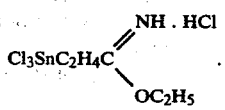

EXAMPLE 17

The reaction of Example 9 is repeated in 100 parts of dimethyl formamide at 60° C. The time taken until saturation with HCl is complete is 2½ hours. The solid residue consists of the compound of Example 9.

EXAMPLE 18

The procedure of Example 9 is repeated in 80 parts of cyclohexane as solvent. At a reaction temperature of 55° C., the time taken until saturation with HCl is complete is 2½ hours. The $^1$NMR spectrum shows that the residue consists in the main of the desired diorgano-tin compound with iminoester function in addition to the analogous amide-containing organotin compound.

EXAMPLE 19

The procedure of Example 9 is repeated in 80 parts of toluene as solvent and saturation with HCl is complete after 4 hours at 55° C. In addition to the diorgano-tin dihalide with iminoester function, the corresponding monoorgano-tin triahlide compound can also be detected in the residue.

EXAMPLE 20

The reaction of Example 9 is repeated in 100 parts of chloroform and 43.3 parts of benzyl alcohol are used instead of ethanol. The reaction is complete after 6 hours at 45°–50° C. The $^1$NMR spectrum shows that

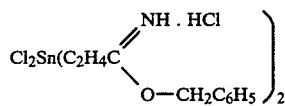

is detectable in the residue. It contains the corresponding monoorgano-tin trihalide and organo-tin halides which contain amido groups.

EXAMPLE 21

Example 20 is repeated with 37.6 parts of phenol instead of benzyl alcohol, affording a compound mixture which has a composition similar to that of Example 20 but which, in comparison, contains a substantially smaller amount of organo-tin halides which contain amido groups.

What is claimed is:

1. A process for the production of organotin compounds of the formula

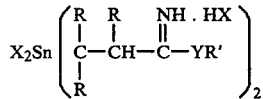

wherein

X represents a chlorine, bromine, or iodine atom,

Y represents an oxygen atom,

R is selected from the group consisting of a hydrogen atom and alkyl, and

R' represents a hydrocarbon group of aliphatic or aromatic character, or said group substituted by a hydroxyl, thiol, alkoxy, alkylthio, carboxyl or carboalkoxy group, which comprises reacting, at −30° C. to +150° C., metallic tin with hydrogen chloride, hydrogen bromide or hydrogen iodide and an unsaturated nitrile of the formula

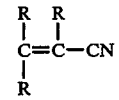

in a reactant medium consisting of an alcohol (R'OH) wherein the molar ratio of alcohol to nitrile is between 1.2:1 to 1:1.

2. A process according to claim 1 wherein R is selected from the group consisting of a hydrogen atom and methyl.

3. A process according to claim 2 wherein R is hydrogen.

4. A process according to claim 1, wherein X represents a chlorine atom.

5. A process according to claim 1, wherein the hydrocarbon group contains 1 to 12 carbon atoms.

6. A process according to claim 5, wherein the hydrocarbon group is linear or branched alkyl or cycloalkyl.

7. A process according to claim 1, wherein the unsaturated nitrile is acrylonitrile, methacrylonitrile, crotonitrile or β-dimethylacrylonitrile.

8. A process according to claim 1, wherein the reaction is carried out without or in the presence of a polar solvent having ether, carboxylic acid ester or sulphone function.

9. A process according to claim 1, wherein the reaction is carried out at a temperature of 20° to 90° C., and under normal or slight excess pressure.

10. A process for the production of organotin compounds of the formula

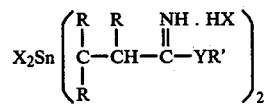

wherein X, R and R' are defined as in claim 1 and Y is a sulfur atom, which comprises reacting, in essentially stoichiometric molar amounts, a compound made by the process according to claim 1 with a mercaptan (R'SH).

* * * * *